(12) United States Patent
Panwar

(10) Patent No.: US 9,743,951 B1
(45) Date of Patent: Aug. 29, 2017

(54) CIRCUMCISION GUARD APPARATUS

(71) Applicant: Monica Panwar, Huntington, WV (US)

(72) Inventor: Narpat Panwar, South Wlliamson, KY (US)

(73) Assignee: Monica Panwar, Huntington, WV (US)

( * ) Notice: Subject to any disclaimer, the term of this patent is extended or adjusted under 35 U.S.C. 154(b) by 45 days.

(21) Appl. No.: 14/803,259

(22) Filed: Jul. 20, 2015

(51) Int. Cl.
*A61B 17/32* (2006.01)
*A61B 17/326* (2006.01)

(52) U.S. Cl.
CPC .................................. *A61B 17/326* (2013.01)

(58) Field of Classification Search
CPC .................................... A61B 17/326
See application file for complete search history.

(56) References Cited

FOREIGN PATENT DOCUMENTS

CN WO 2005039424 A1 * 5/2005 ........... A61B 17/326

* cited by examiner

*Primary Examiner* — Ashley Fishback
(74) *Attorney, Agent, or Firm* — Williams Intellectual Property; Benjamin F. Williams

(57) ABSTRACT

A circumcision guard apparatus that includes a flexible, durable disc having an aperture centrally disposed therein, said aperture congruent with an open channel disposed radially between said aperture and the circumference of the disc, wherein manual action applied across the open channel effects spearation of the disc at the aperture, whereby the disc is fittable to gird a patient's penis proximal the prepuce and glans, and thereby shield and protect proximal tissue from inadvertant contact with a surgeon's blade during the act of circumcision.

5 Claims, 1 Drawing Sheet

CIRCUMCISION GUARD APPARATUS

BACKGROUND OF THE INVENTION

Various types of medical apparatuses usable to protect a patient against inadvertant harm during surgery are known in the prior art. However, what is needed is a circumcision guard apparatus that includes a flexible, durable disc, readily fittable around a patient's penis and there radially dispositional to guard and shield tissue proximal the patient's glans from inadvertent contact with a surgeon's blade during the act of circumcision.

FIELD OF THE INVENTION

The present invention relates to a circumcision guard apparatus, and more particularly, to a circumcision guard apparatus that includes a flexible, durable disc having an aperture centrally disposed therein, said aperture congruent with an open channel disposed radially between said aperture and the circumference of the disc, wherein manual action applied across the open channel effects further spearation of the disc at the aperture, whereby the disc is fittable to gird a patient's penis proximal the prepuce and glans, and thereby shield and protect proximal tissue from inadvertent contact with a surgeon's blade during the act of circumcision.

SUMMARY OF THE INVENTION

The general purpose of the circumcision guard apparatus, described subsequently in greater detail, is to provide a circumcision guard apparatus which has many novel features that result in a circumcision guard apparatus which is not anticipated, rendered obvious, suggested, or even implied by prior art, either alone or in combination thereof.

The present circumcision guard apparatus has been devised to enable securable position of a flexible, durable disc circumferentially girding a patient's penis to shield the patient proximal the glans and thus prevent inadvertent injury during the act of circumcision.

The present circumcision guard apparatus, therefore, includes a flexible, durable disc, fittable around a patient's penis to shield tissue proximal the glans and prevent accidental injury thereto during the act of circumcision.

The flexible, durable disc includes a top surface and a bottom surface. An aperture is disposed centrally in the disc, said aperture connected to an open channel disposed radially between the aperture and an open end disposed at the circumference of the disc. The open channel diverges from a minimum gap, at the aperture, to a maximum gap at the disc circumference.

The aperture is separable by manual action applied across the open channel, whereby the aperture is fittable around the penis of a patient about to undergo circumcision. Once the patient's penis is positioned into the aperture, the disc is thereby situated radially surrounding the penis and serves to shield and protect the tissue proximal the glans and prepuce from inadvertent contact with a surgeon's blade during the act of circumcision.

A conformable, congruent edge may be disposed bounding the open channel and aperture, whereby contact of the disc with the penis is enabled without causing discomfort to the patient.

Thus has been broadly outlined the more important features of the present circumcision guard apparatus so that the detailed description thereof that follows may be better understood and in order that the present contribution to the art may be better appreciated.

Objects of the present circumcision guard apparatus, along with various novel features that characterize the invention are particularly pointed out in the claims forming a part of this disclosure. For better understanding of the circumcision guard apparatus, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
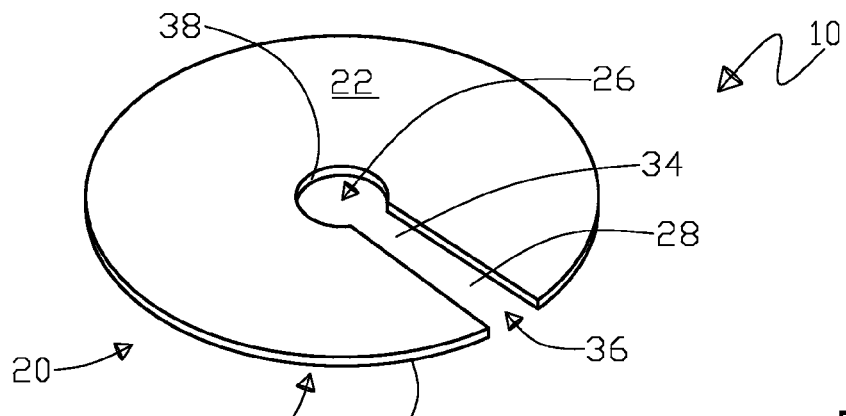
FIG. 1 is an isometric elevated view of an embodiment.
Figure 2:
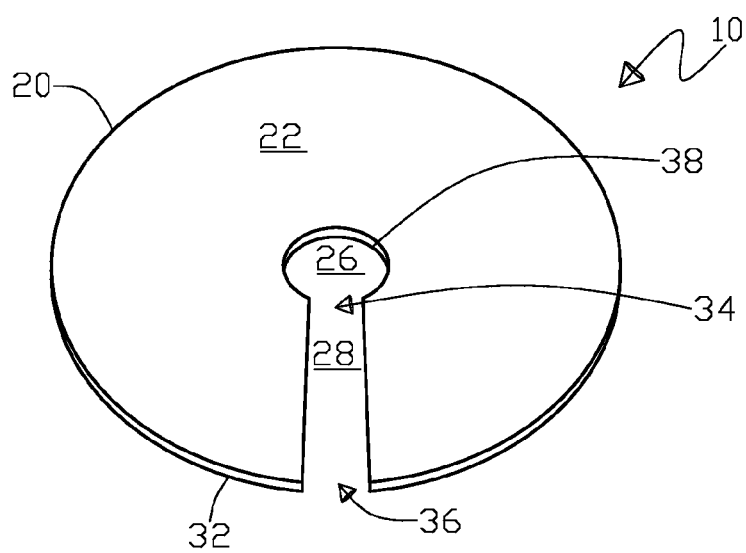
FIG. 2 is a top view of an embodiment.
Figure 3:
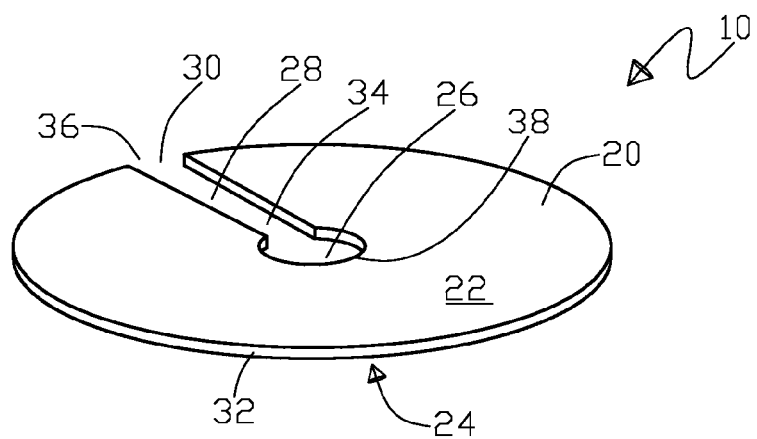
FIG. 3 is an isomeric view of an embodiment.

With reference now to the drawings, and in particular FIGS. 1 through 3 thereof, example of the instant circumcision guard apparatus employing the principles and concepts of the present circumcision guard apparatus and generally designated by the reference number 10 will be described.

Referring to FIGS. 1 through 3 a preferred embodiment of the present circumcision guard apparatus 10 is illustrated.

The present circumcision guard apparatus 10 has been devised to enable protective engagement around the penis of a patient undergoing circumcision. The present circumcision guard apparatus 10 includes a flexible, durable disc 20 fittable around the penis of a patient to position a protective barrier proximal the glans of the patient, whereby a surgeon's blade is prevented from inadvertent contact with tissue proximal the glans of the patient and accidental injury is thereby preventable.

The present circumcision guard apparatus 10, therefore, includes a polymeric, flexible, durable disc 20 having a top surface 22 and a bottom surface 24. An aperture 26 is disposed centrally within the disc 20 and an open channel 28 is disposed radially from the aperture 26 to terminate at an open end 30 disposed at a section of the disc circumference 32. The open channel 28 diverges, from a minimum gap 34 disposed at the aperture 26 towards a maximum gap 36 disposed at the disc circumference 32. To prevent discomfort, a conformable congruent edge 38 is disposed within the disc 20 bounding the aperture 26 and the open channel 28 in position to engage against a patient's penis.

The disc 20 is pliable and the aperture 26 is further separable by opposable action engaged across the open channel 28 in a plane normal the top surface 22 of the disc 20, whereby the disc 20 is fittable around the penis of a patient about to undergo circumcision. The disc 20 is thereby positional to shield and protect tissue of the patient proximal the prepuce and glans of said patient's penis during the act of circumcision.

What is claimed is:
1. A circumcision guard apparatus comprising:
a flexible, durable disc;
an aperture disposed centrally within the disc; and an open channel disposed radially from the aperture, said open channel terminating at an open end at the disc circumference;

wherein the disc is fittable around the penis of a patient to protect tissue of the patient proximal the prepuce and glans of said patient's penis during the act of circumcision.

2. The circumcision guard apparatus of claim 1 wherein the open channel diverges from a minimum gap disposed most proximal the aperture towards a maximum gap disposed at the disc circumference.

3. The circumcision guard apparatus of claim 2 wherein the disc is fittable around the penis of a patient by plying the disc at the open channel wherein the aperture is further widened for position of the penis within the aperture, wherein release of the disc returns the aperture to its former size at the minimum gap, whereby the disc engages around the patient's penis.

4. The circumcision guard apparatus of claim 3 wherein the aperture and open channel include a conformable congruent edge disposed within the disc for engagement against the penis of the patient.

5. A circumcision guard apparatus comprising:

a flexible, durable disc having a top surface and a bottom surface;

an aperture disposed centrally within the disc;

an open channel disposed radially from the aperture, said open channel terminating at the disc circumference, said open channel diverging from a minimum gap disposed at the aperture towards a maximum gap disposed at the disc circumference; and a conformable congruent edge disposed within the disc bounding the aperture and the open channel in position to engage against a patient's penis;

wherein the disc is pliable and the aperture is further separable by opposable action engaged across the open channel in a plane normal the top surface of the disc, whereby the disc is fittable around the penis of a patient and there positionable to shield and protect surrounding tissue of the patient proximal the prepuce and glans of said patient's penis during the act of circumcision.

* * * * *